United States Patent
Hansson et al.

(10) Patent No.: US 11,602,382 B2
(45) Date of Patent: Mar. 14, 2023

(54) DEVICE FOR FIXATION OF BONE FRAGMENTS

(71) Applicant: SWEMAC INNOVATION AB, Linköping (SE)

(72) Inventors: Henrik Hansson, Vreta Kloster (SE); Lars Öster, Lidköping (SE)

(73) Assignee: SWEMAC INNOVATION AB, Linkoping (SE)

( * ) Notice: Subject to any disclaimer, the term of this patent is extended or adjusted under 35 U.S.C. 154(b) by 28 days.

(21) Appl. No.: 17/048,645

(22) PCT Filed: Apr. 27, 2018

(86) PCT No.: PCT/EP2018/060903
§ 371 (c)(1),
(2) Date: Oct. 19, 2020

(87) PCT Pub. No.: WO2019/206431
PCT Pub. Date: Oct. 31, 2019

(65) Prior Publication Data
US 2021/0236181 A1    Aug. 5, 2021

(51) Int. Cl.
*A61B 17/74* (2006.01)
*A61B 17/72* (2006.01)
*A61B 17/86* (2006.01)

(52) U.S. Cl.
CPC ........ *A61B 17/746* (2013.01); *A61B 17/7225* (2013.01); *A61B 17/7241* (2013.01); *A61B 17/863* (2013.01); *A61B 17/8685* (2013.01)

(58) Field of Classification Search
CPC .............. A61B 17/746; A61B 17/7225; A61B 17/7241; A61B 17/863; A61B 17/8685
(Continued)

(56) References Cited

U.S. PATENT DOCUMENTS 4,488,543 A * 12/1984 Tornier ................ A61B 17/746
                                                            606/65
8,454,665 B2 * 6/2013 Sidebotham ....... A61B 17/8863
                                                            606/280
(Continued)

FOREIGN PATENT DOCUMENTS

JP    2000515041 A    11/2000
JP    2010523295 A    7/2010
(Continued)

OTHER PUBLICATIONS

Japanese Office Action for corresponding Japanese Application Serial No. 2020-560161, dated Dec. 24, 2021, pp. 1-6.

*Primary Examiner* — Eduardo C Robert
*Assistant Examiner* — David C Comstock
(74) *Attorney, Agent, or Firm* — Tarolli, Sundheim, Covell & Tummino LLP

(57) ABSTRACT

A device for fixation of inner and outer bone fragments comprises at least three fixation means (5), at least one tilting preventing means (6) and a securing plate (7). The fixation means (5) are configured to allow, during secondary compression of the inner and outer bone fragments (2, 3), a sliding movement of the fixation means and said outer bone fragment relative to one another and thereby an interruption of an engagement of the securing plate (7) with the outer bone fragment (3) without affecting the angular position of the fixation means relative to the securing plate and relative to one another. The tilting preventing means (6) is configured to allow, during said secondary compression, a sliding movement of the at least one tilting preventing means and said outer bone fragment (3) relative to one another and thereby an interruption of the engagement of the securing plate (7) with the outer bone fragment. The tilting preventing (Continued)

means (6) is also configured to prevent or counteract tilting of the device.

12 Claims, 6 Drawing Sheets

(58) Field of Classification Search
USPC ..... 606/65, 67, 70, 280, 282, 286, 291, 308, 606/316
See application file for complete search history.

(56) References Cited

U.S. PATENT DOCUMENTS

| | | | | |
|---|---|---|---|---|
| 9,642,657 | B2* | 5/2017 | Hansson | A61B 17/746 |
| 2005/0010226 | A1* | 1/2005 | Grady | A61B 17/809 |
| | | | | 606/281 |
| 2005/0015089 | A1* | 1/2005 | Young | A61B 17/8014 |
| | | | | 606/915 |
| 2005/0085818 | A1 | 4/2005 | Huebner | |
| 2006/0036248 | A1* | 2/2006 | Ferrante | A61B 17/725 |
| | | | | 606/64 |
| 2006/0264947 | A1* | 11/2006 | Orbay | A61B 17/1684 |
| | | | | 606/291 |
| 2009/0157123 | A1 | 6/2009 | Appenzeller et al. | |
| 2010/0152783 | A1* | 6/2010 | Borostyankoi | A61B 17/8014 |
| | | | | 606/281 |
| 2010/0217332 | A1 | 8/2010 | Daniels et al. | |
| 2010/0249850 | A1* | 9/2010 | Cerynik | A61B 17/86 |
| | | | | 606/281 |
| 2011/0224734 | A1* | 9/2011 | Schelling | A61B 17/7079 |
| | | | | 606/286 |
| 2011/0264150 | A1* | 10/2011 | Hansson | A61B 17/746 |
| | | | | 606/290 |
| 2014/0378973 | A1 | 12/2014 | Mueckter | |
| 2018/0177538 | A1 | 6/2018 | Hansson | |
| 2018/0221066 | A1* | 8/2018 | Grusin | A61B 17/8685 |

FOREIGN PATENT DOCUMENTS

| | | |
|---|---|---|
| JP | 2016195837 A | 11/2016 |
| JP | 201815574 A | 2/2018 |
| WO | 9802105 | 1/1998 |
| WO | 2017/007382 A1 | 1/2017 |

* cited by examiner

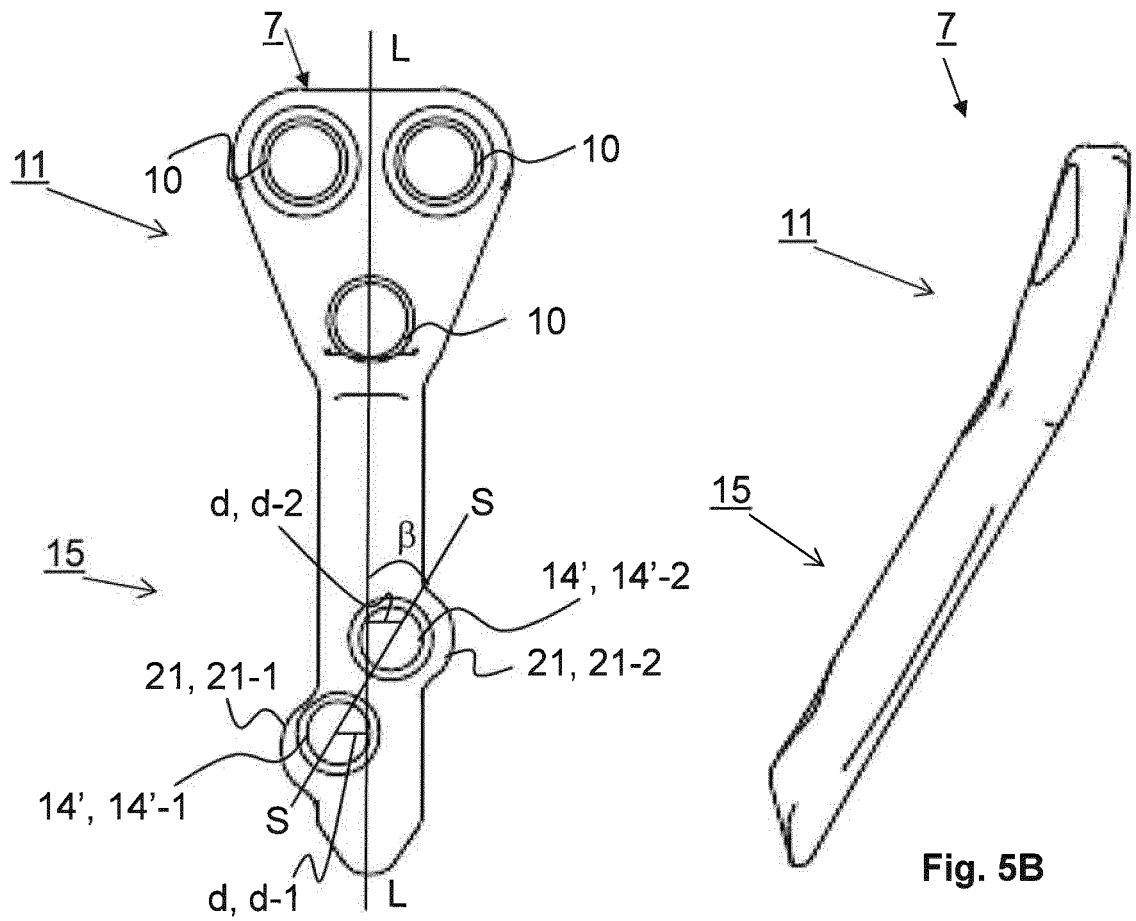
Fig. 5A
Fig. 5B
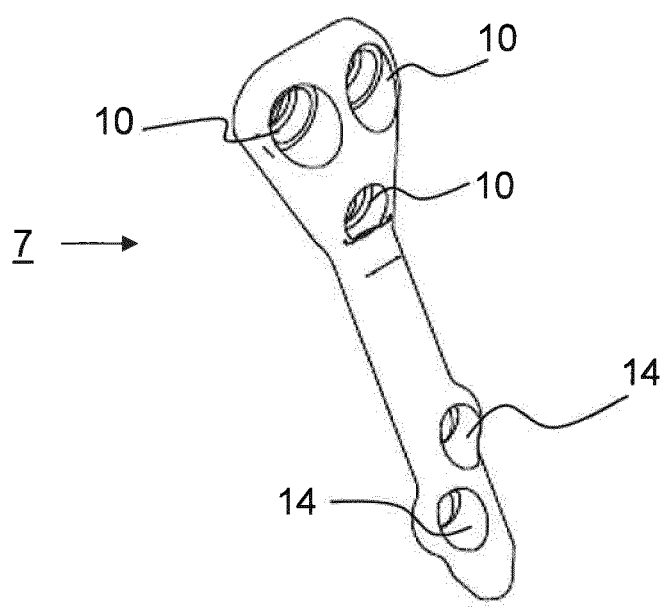
Fig. 5C

DEVICE FOR FIXATION OF BONE FRAGMENTS

RELATED APPLICATION

This application corresponds to PCT/EP2018/060903, filed Apr. 27, 2018, the subject matter of which is incorporated herein by reference in its entirety.

TECHNICAL FIELD

Embodiments disclosed herein relate to a device for fixation of bone fragments at bone fractures.

BACKGROUND

After a bone fracture such as a femur neck fracture, the bone fragments at the fracture need fixing. This is currently done by using suitable fixation means, e.g. bone nails or bone screws.

After the completion of surgery, even as early as when the effects of the anaesthesia have passed and the patient is still confined to bed, but above all when the patient is beginning to be up and walk and stand on the leg, the fixed bone fragments and the fixation means are subject to large forces, particularly to rotational forces acting downwards and rearwards.

The fixation means alone are often insufficient to counteract these rotational forces and the bone fragments have to be used to help to lock the fracture. If this is not done and the bone fragments are caused to rotate relative to one another by said forces, the result will be shifting of the angular positions of the fixation means to such an extent that they risk substantially crossing one another, thereby keeping the fracture parted and preventing healing.

Another problem at many types of bone fractures, e.g. vertical femoral neck fractures such as Pauwel III where the obliquity of the fracture line with the horizontal plane is 70° or more, is that one or more of the bone fragments due to the character of such fractures tend to tilt (varus tilting).

SUMMARY

The above-mentioned problems can at least partly be prevented or counteracted by configuring the device in such a way that the fixation means are not allowed to rotate and cross one another.

To this end, the device according some embodiments comprises at least three fixation means and a securing plate. The at least three fixation means each comprises a first fixing portion which is configured for fixing the fixation means in an inner bone fragment, and a second fixing portion with threads for locking the fixation means in substantially parallel holes with threads in a first end portion of the securing plate. The securing plate is configured for engagement of an outside surface of an outer bone fragment without a fixed connection therewith. Each fixation means also comprises a middle portion which is situated between the first and second fixing portions. This middle portion is configured to run through the outer bone fragment. It is also configured to allow, during secondary compression of the inner and outer bone fragments due to forces, particularly downwardly and rearwardly directed rotational forces, applied thereto, a sliding movement of the at least three fixation means and said outer bone fragment relative to one another and thereby an interruption of the engagement of the securing plate with the outer bone fragment without affecting the angular position of the fixation means relative to the securing plate and relative to one another.

The result of the fixation means being thus fixed to the inner bone fragment and to the securing plate while the outer bone fragment, relatively seen, can move towards the inner bone fragment and, in so doing, be guided by the fixation means, is that the bone fragments are kept fixed but (secondary) compression of the bone fragments is nevertheless allowed, the device and the bone fragments thus being able to absorb the aforesaid rotational forces and control them so that no redislocation occurs. The fixing of the fixation means in the inner bone fragment and the locking of the fixation means to the securing plate also reduce the risk of screws loosening in cases where the fixation means take the form of bone screws.

To prevent or counteract tilting, the device according to some embodiments further comprises at least one tilting preventing means. This at least one tilting preventing means comprises a fixing portion with threads for locking the tilting preventing means in a hole with threads in a second end portion of the securing plate opposite to said first end portion thereof. This hole in the second end portion of the securing plate is substantially parallel with the holes for the fixation means in the first end portion of the securing plate. The at least one tilting preventing means also comprises an engagement portion which is configured to extend into the outer bone fragment without a fixed connection therewith and configured to allow, during said secondary compression of the inner and outer bone fragments, a sliding movement of the at least one tilting preventing means and said outer bone fragment relative to one another and thereby an interruption of the engagement of the securing plate with the outer bone fragment. The engagement portion of the tilting preventing means also prevents or counteracts, by means of the part thereof remaining in the outer bone fragment after possible sliding movement of the tilting preventing means relative to the outer bone fragment, tilting of the device due to forces trying to cause such tilting, particularly varus tilting, of the inner bone fragment.

Other objects and advantages will be apparent to one skilled in the art who examines the attached drawings and the following detailed description of preferred embodiments of and method for fitting the device.

BRIEF DESCRIPTION OF THE DRAWINGS

Some embodiments will hereinafter be further explained by means of a non-limiting example with reference to the accompanying drawings, in which

FIGS. 5A, 5B and 5C are schematic views of some alternative embodiments of a securing plate.

It should be noted that the accompanying drawings are not necessarily drawn to scale and that the dimensions of some features of the shown embodiments may have been exaggerated for the sake of clarity.

DETAILED DESCRIPTION OF PREFERRED EMBODIMENTS

The present invention will in the following be exemplified by embodiments thereof. It should however be realized that the embodiments are included to explain principles of the invention and not to limit the scope of the invention as defined by the appended claims.

Figure 1A:
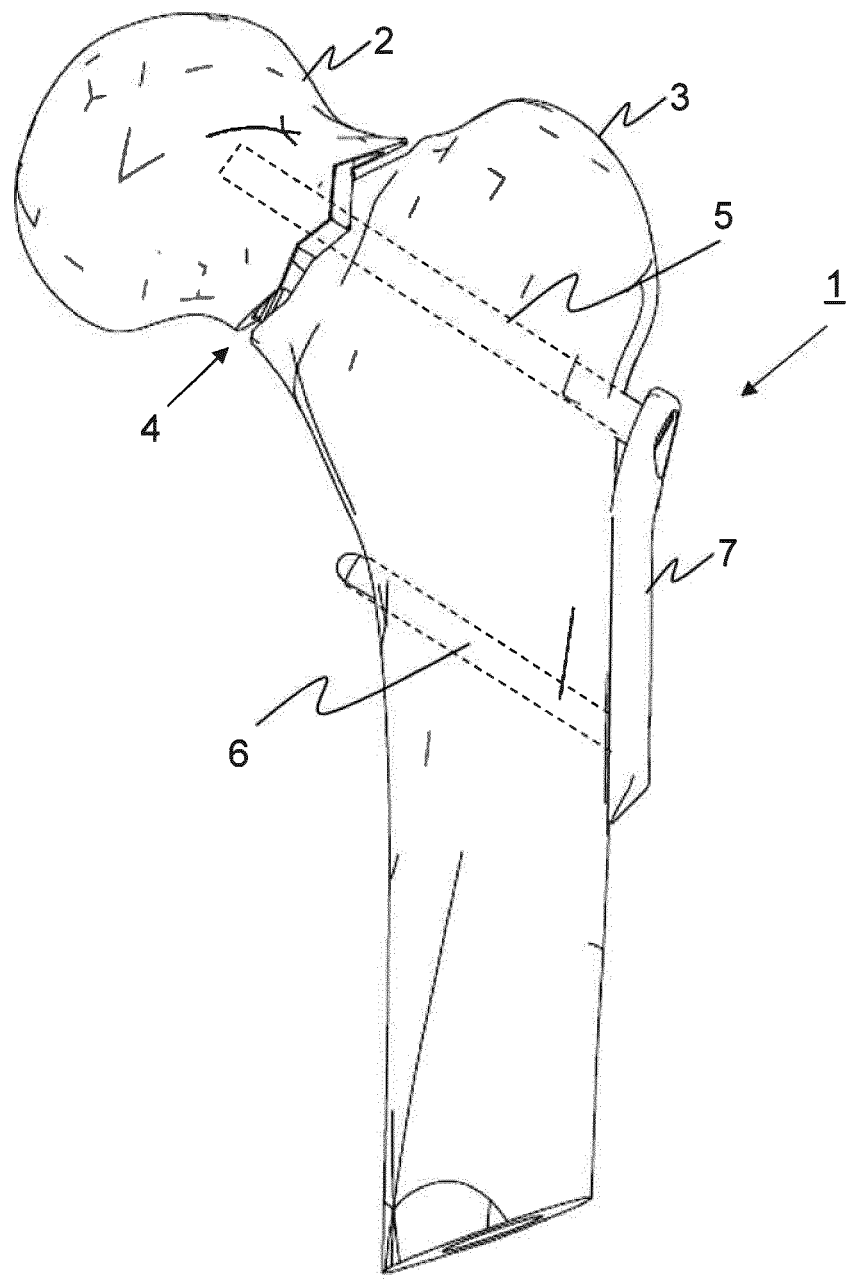
FIG. 1A is a schematic longitudinal section through upper portions of a femur with a fracture at the neck of the femur and provided with a device according to embodiments.

Thus, as already mentioned, embodiments relate to a device 1 for fixation of inner and outer bone fragments 2 and 3 at bone fractures 4. In the embodiment of FIG. 1A, the bone fracture is a substantially vertical femoral neck fracture 4 classified as Grade III according to Pauwel. Thus, we have an inner bone fragment 2 in the form of the femoral head on one side of the fracture 4 and an outer bone fragment 3 in the form of the femur except the femoral head on the other side of the fracture. Other bone fractures where the device according some embodiments may be useful are e.g. fractures where there is no support from inferior cortex, basicervical fractures and possibly also stable intertrochanteric fractures.

Figure 1B:
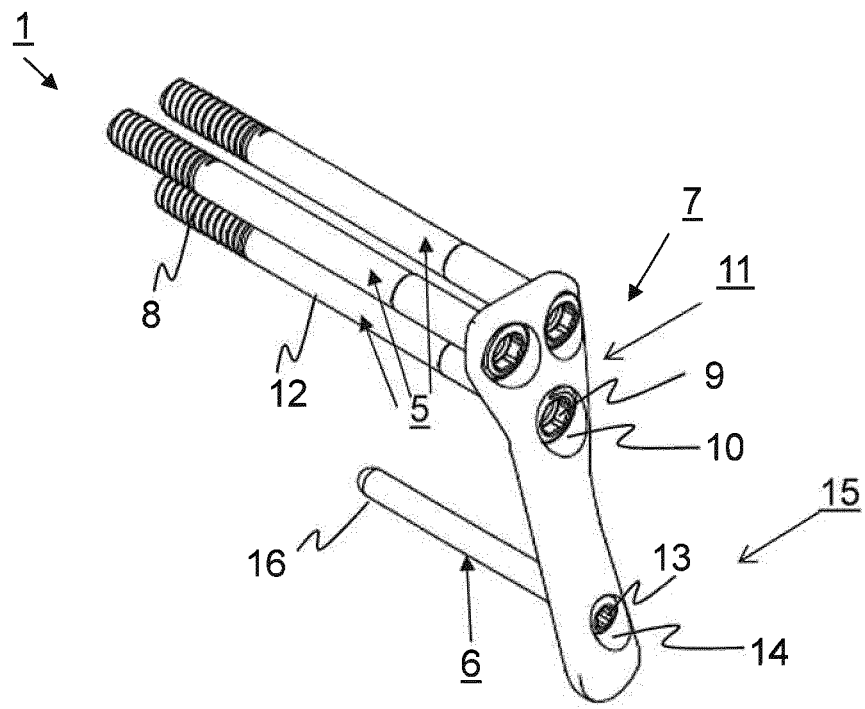
FIG. 1B is a schematic perspective view of a first embodiment of a device for fixation of bone fragments.
Figure 1C:
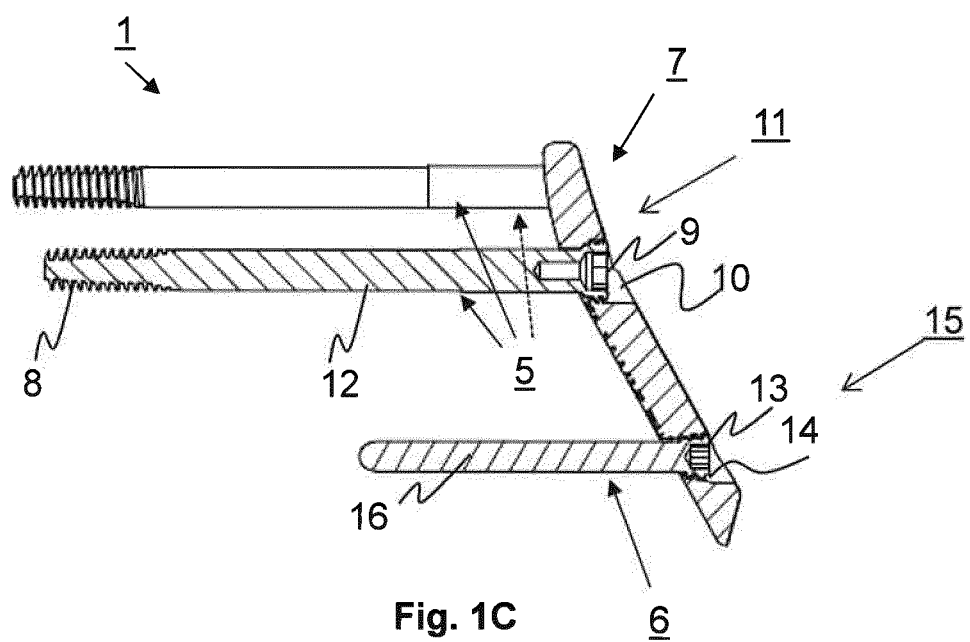
FIG. 1C is a schematic sectional side view of the device of FIG. 1B.

As schematically illustrated in FIGS. 1B and 1C, the device 1 comprises, according to some embodiments, at least three fixation means 5 in the form of bone screws or bone nails, in the illustrated embodiment three bone screws, at least one tilting preventing means 6, in the illustrated embodiment one tilting preventing means in the form of a peg, and a securing plate 7. It should be understood that in the view shown in FIG. 1C, two of the fixation means 5 are located in the same plane and thus only one of the is shown.

The securing plate 7 is configured for engagement of an outside surface, e.g. the lateral side as illustrated, of the outer bone fragment 3 without a fixed connection therewith, i.e. the securing plate allows movement thereof and of the outer bone fragment relative to each other, such that the securing plate 7 will not move with the outer bone fragment upon secondary compression of the inner and outer bone fragments 2, 3 due to forces, particularly downwardly and rearwardly directed rotational forces, applied thereto. This is accomplished while each of the at least three fixation means 5 comprises a first fixing portion 8 which is configured fixing the fixation means 5 in the inner bone fragment 2, i.e. the femoral head, and while each fixation means 5 also comprises a second fixing portion 9 with threads for locking the fixation means 5 in one of a number of holes 10 with threads therefor in a first end portion 11 of the securing plate 7. Finally, each fixation means 5 comprises a middle portion 12 which is situated between the first and second fixing portions 8, 9. This middle portion 12, having a smooth unthreaded exterior, is configured to run through the outer bone fragment 3. Consequently, the middle portion 12 is also configured to allow, during secondary compression of the inner and outer bone fragments 2, 3, a sliding movement of each fixation means 5 and the outer bone fragment 3 relative to each other. Thereby, as a consequence of that the securing plate 7 is locked to the fixation means 5, the engagement of the securing plate with the outer bone fragment 3 will be interrupted without affecting the angular position of the fixation means 5 relative to the securing plate and 7 relative to one another. The sliding movement may cause the securing plate 7 to be moved a distance of approximately 5 mm from the outer bone fragment 3. Thus, the sliding movement may give rise to a gap of approximately 5 mm between the securing plate 7 and the outer bone fragment 3.

The at least one tilting preventing means 6 of the device 1 comprises a fixing portion 13 with threads for locking the tilting preventing means 6 in a hole 14 with threads in a second end portion 15 of the securing plate 7 opposite to said first end portion 11 thereof. This hole 14 in the second end portion 15 of the securing plate 7 is substantially parallel with the holes 10 for the fixation means 5 in the first end portion 11 of the securing plate 7. The at least one tilting preventing means 6 also comprises an engagement portion 16 which is configured to extend into the outer bone fragment 3 without a fixed connection therewith. The engagement portion 16 is also configured to allow, during said secondary compression of the inner and outer bone fragments 2, 3, a sliding movement of the at least one tilting preventing means 6 and said outer bone fragment 3 relative to one another and thereby cause an interruption of the engagement of the securing plate 7 with the outer bone fragment 3, i.e. it is configured to provide for the same result as the middle portion 12 of the fixation means 5. The engagement portion 16 of the tilting preventing means 6 also prevents or counteracts, by means of the part thereof remaining in the outer bone fragment 3 after possible sliding movement of the tilting preventing means 6 relative to the outer bone fragment 3, tilting of the device 1 due to forces trying to cause such tilting, particularly varus tilting, of the inner bone fragment 2.

By the expression "secondary compression" when used in this disclosure is meant a compression of the inner and outer bone fragments 2, 3 due to forces, particularly downwardly and rearwardly directed rotational forces, applied thereto after surgery. For example, when the patient is beginning to be up and walk and stand on the leg, the fixed bone fragments and the fixation means 5 are subject to large forces, particularly to rotational forces acting downwards and rearwards, causing the secondary compression of the inner and outer bone fragments 2, 3. The secondary compression is a compression in addition to a primary compression caused by the device 1 for fixation.

In order to improve the tilting preventing or tilting counteracting effect, the engagement portion 16 of the at least one tilting preventing means 6 may be configured to run through the outer bone fragment 3 from one side thereof to the opposite side, in the illustrated embodiment from the lateral side of the outer bone fragment 3 to the opposite medial side, cf. FIG. 1A. Since the at least one tilting preventing means 6 when in use in this scenario runs through both the lateral cortex of the outer bone fragment 3 and the medial cortex of the outer bone fragment 3, the fixation may be referred to as a bicortical fixation. Preferably, the tilting preventing means 6 is thereby configured with such length, e.g. in the range of 60-70 mm, that it can run through the outer bone fragment 3 from the lateral side thereof to the opposite medial side and also protrude therefrom by e.g. about 4-8 mm or 5-10 mm. Thereby, you have support not only at the entrance site for the tilting preventing means 6 into the outer bone fragment 3, but also at least at the opposite exit site and preferably also the entire distance through the outer bone fragment 3, such that tilting forces applied to said tilting preventing means 6 can be distributed over and thus, taken up and neutralized by a larger surface of the outer bone fragment 3. When using only one tilting preventing means 6, the securing plate 7 may be configured with a shorter length as compared to the case when the securing plate 7 comprises two or more tilting preventing means 6.

However, it should be understood that the device 1 may be used for so called unicortical fixation wherein the one or more tilting preventing means 6, when in use, only runs through the lateral cortex of the outer bone fragment 3 and thus does not extend into the medial cortex of the outer bone fragment 3. In this scenario, the length of the tilting preventing means 6 may be in the range of 20-30 mm, e.g. 24-28 mm. In such embodiments, the front end of the tilting preventing means 6 may in use be located in the medullary cavity of the outer bone fragment 3.

Figure 2A:
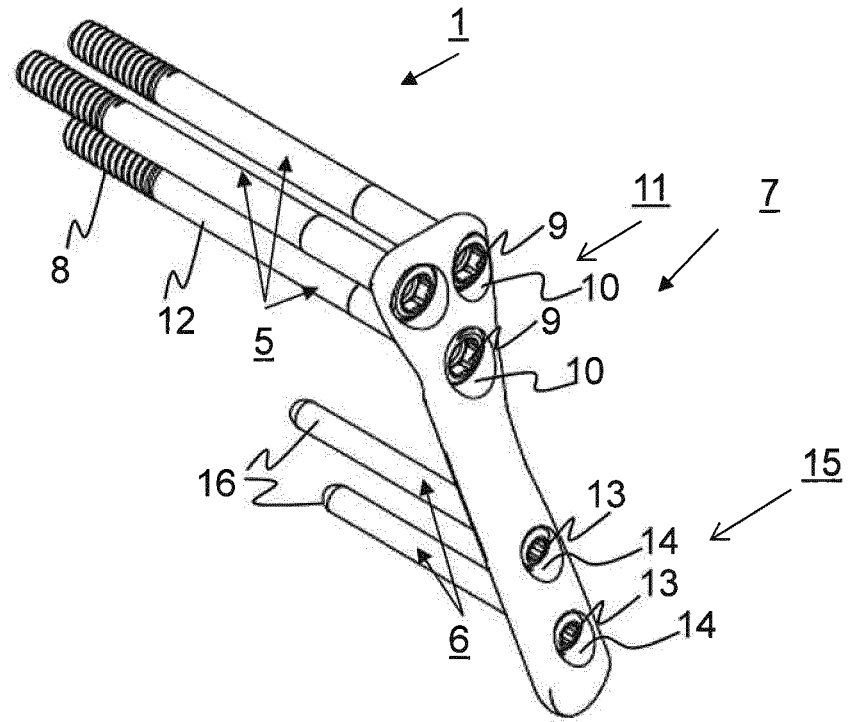
FIG. 2A is a schematic perspective view of a second embodiment of a device for fixation of bone fragments.
Figure 2B:
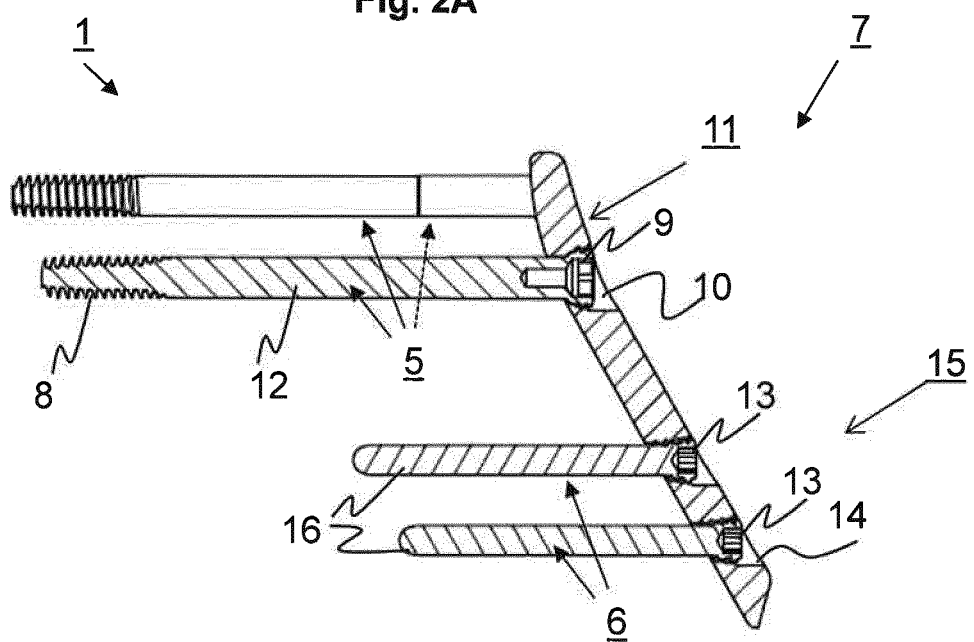
FIG. 2B is a schematic sectional side view of the device of FIG. 2A.

The device may as illustrated in FIGS. 1A-1C comprise one tilting preventing means 6 or may as illustrated in FIGS. 2A and 2B comprise two tilting preventing means 6. The securing plate 7 is accordingly configured with one and two threaded holes 14 respectively, for the tilting preventing means 6. It should be understood that in the view shown in FIG. 2B, two of the fixation means 5 are located in the same plane and thus only one of the is shown.

When the device 1 is configured to comprise two tilting preventing means 6, the length of each tilting preventing means 6 may, in some embodiments and as mentioned above, be in the range of 20-30 mm, e.g. 24-28 mm. Thereby, the tilting preventing means 6 will not extend into the medial cortex when in use but will only be arranged in the lateral cortex and in the medullary cavity. This means a simplified fixation procedure since the surgeon does not have to measure the distance from the lateral cortex to the medial cortex. When using a short tilting preventing means 6 configured for unicortical fixation, the device 1 is preferably configured to comprise two tilting preventing means 6, as shown in FIG. 2A or 2B, or even more tilting preventing means 6 in order to provide sufficient stability and to prevent varus tilting.

As mentioned above, the tilting preventing means 6 is in the drawings illustrated as a peg and said peg is configured with a threaded end portion which constitutes the fixing portion 13. The tilting preventing means 6 may of course be configured in any other suitable manner for its object and purpose.

Figure 3A:
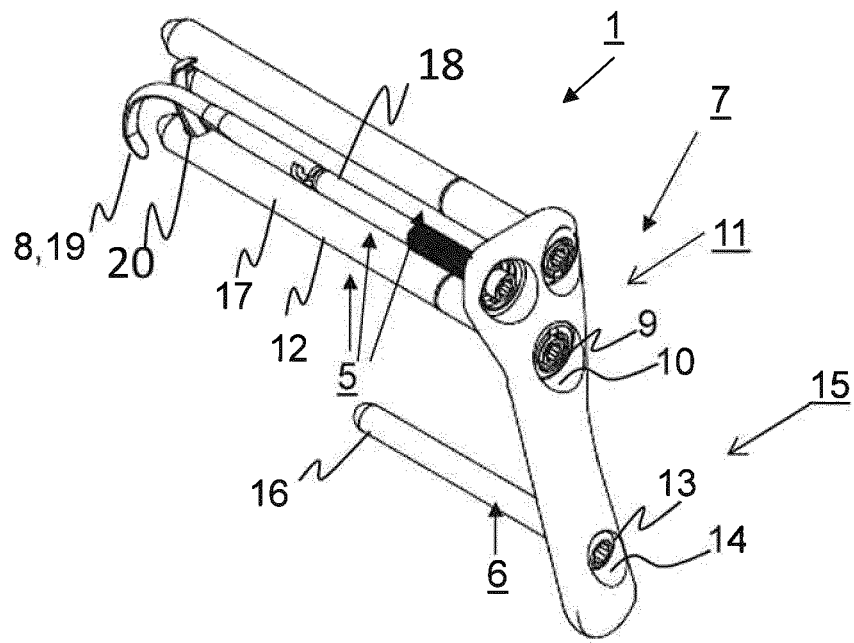
FIGS. 3A and 3B are schematic perspective views of some third embodiments of a device for fixation of bone fragments.
Figure 3B:
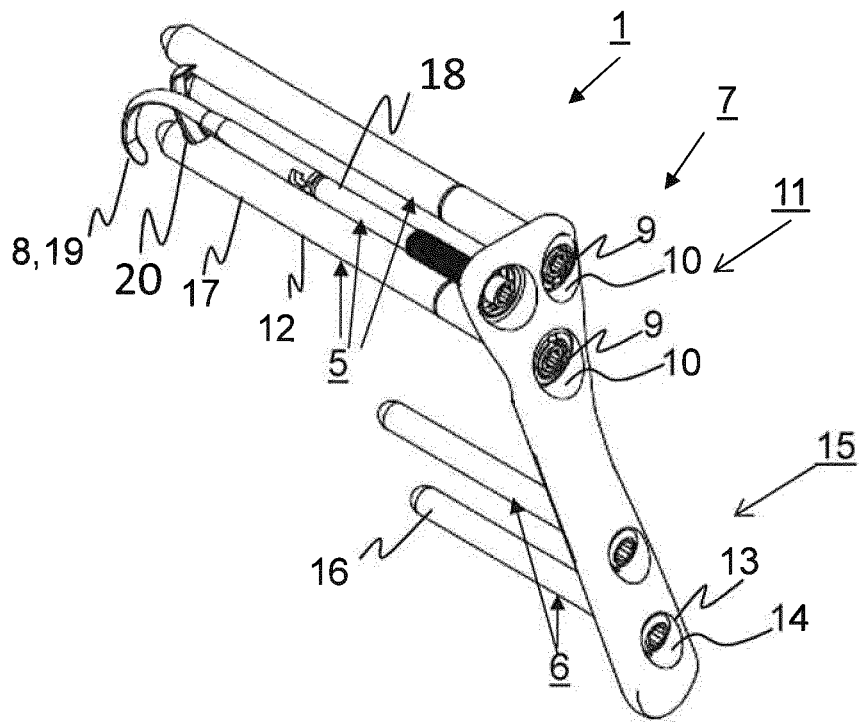

As mentioned above, the fixation means 5 may as illustrated in FIGS. 1-2 consist of bone screws with a first fixing portion 8 in the form of a threaded forward end portion of the bone screw, but may alternatively consist of bone nails, as schematically illustrated in FIGS. 3A and 3B. These bone nails may comprise a sleeve 17 and, disposed therein, a pin 18 arranged for movement in the sleeve 17 so that at least a forward portion 19 of the pin 18 can be driven outwards through at least one lateral aperture 20 in the sleeve, in which case this forward portion constitutes a first fixing portion 8 in the form of at least one hook which engages in the inner bone fragment 2, and the respective bone nail has in addition a second fixing portion 9 of the type described above. In the FIGS. 3A and 3B one of the fixation means 5 is illustrated without the sleeve 17 in order to illustrate the pin 18. As the density of the inner bone fragment 2 is greatest at its centre, it is of advantage if the respective bone nail is applied in such a way that the forward portion 19 of the pin 18 is caused, during the outward driving thereof, to engage in the central portions of the bone fragment. The respective bone nail may also be so configured as to achieve engagement in the central portions of the inner bone fragment 2. For example, since there is a threaded second fixing portion 9, the threads therein may be so disposed and/or configured that said result is achieved. Having the forward portion 19 of the pin 18 in the respective bone nail pointing towards the centre of the inner bone fragment 2 not only means that the bone nails have a better grip in the inner bone fragment but also counteracts the risk of rotation or other movement of the bone nails.

As illustrated in the drawings, the first end portion 11 of the securing plate 7 has a substantially triangular shape with the threaded holes 10 for the at least three fixation means 5 arranged in a substantially triangular pattern. Rotational forces acting on the bone fragments 2,3 and the fixation means 5 are thereby taken up better. The shape of the first end portion 11 of the securing plate 7 may however have any other suitable shape. The lateral surface of the securing plate 7 facing/engaging the outside (lateral) surface of the outer bone fragment 3 is preferably adapted to the shape of said outside surface; has e.g. a substantially concave lateral surface as illustrated in the drawings.

The threaded holes 10 for the at least three fixation means 5 and the threaded hole or holes 14 for the tilting preventing means 6 in the first and second end portions 11 and 15 respectively, of the securing plate 7, are all configured such that they run obliquely through the securing plate.

Figure 4A:
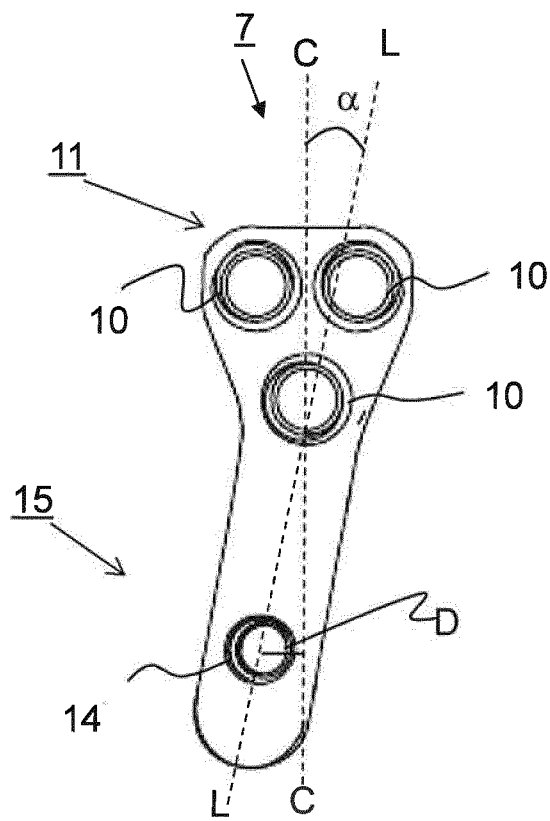
FIGS. 4A, 4B, and 4C are schematic views of some embodiments of a securing plate.
Figure 4B:
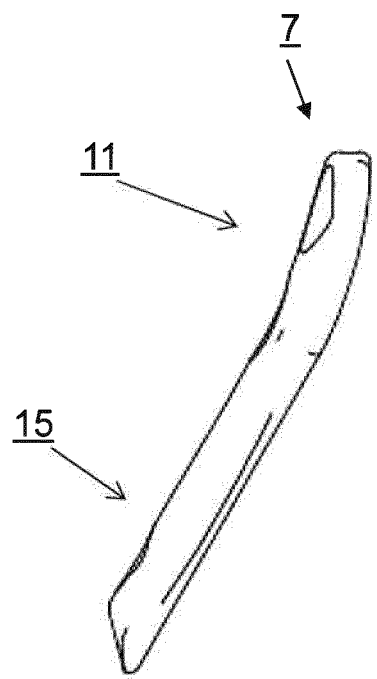
Figure 4C:
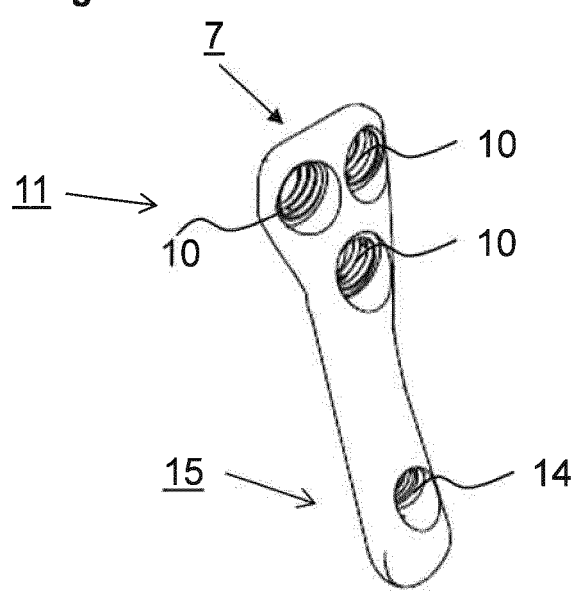

In some embodiments, as for example schematically illustrated in FIGS. 4A-4C, the substantially triangular shape of the first end portion 11 of the securing plate 7 is tilted or angled relative a longitudinal axis L-L of the shaft of the securing plate 7. As illustrated, the first end portion 11 of the securing plate 7 has a triangular shape that is angled an angle α relative to the longitudinal axis L-L of the securing plate 7. The angle α may be in the range of 5 to 15 degrees, and in some embodiments the angle α is about 10 degrees. The threaded holes 10 for the at least three fixation means 5 are arranged in a substantially triangular pattern in the first end portion 11. The second end portion 15 comprises one or more threaded holes 14 for one or more tilting preventing means 6. The longitudinal axis L-L may intersect the center of the one or more threaded holes 14. In FIG. 4A, one threaded hole 14 is illustrated and it is located along the longitudinal axis L-L a distance D of approximately 5 mm from a symmetry axis C-C of the first end portion 11. The one or more threaded holes 10,14 are arranged to run obliquely through the securing plate 7. Preferably, the one or more threaded holes 10,14 are arranged to run obliquely through the securing plate 7 such that the one or more fixation means 5 and the one or more tilting preventing means 6 are parallel with each other when arranged in the respective hole 10,14. This is schematically illustrated in FIGS. 1-3.

In FIGS. 4A and 4C only one threaded hole 14 for one tilting preventing means 6 is illustrated but it should be understood that the number of holes 14 may be more, e.g. two or more. The one or more threaded holes 14 are sometimes in this disclosure referred to as central threaded holes 14 when they are arranged along the longitudinal axis L-L of the securing plate 7.

In some embodiments, as for example schematically illustrated in FIGS. 5A-5C, the securing plate 7 is a straight securing plate 7. That means that the substantially triangular shape of the first end portion 11 of the securing plate 7 is arranged symmetrically around the longitudinal axis L-L of the securing plate 7. Further, in some embodiments, as for example schematically illustrated in FIGS. 5A and 5C, the second end portion 15 of the securing plate 7 may be provided with one or more lateral threaded holes 14' arranged laterally of the longitudinal axis L-L such that the longitudinal axis L-L does not intersect the center of the one or more lateral holes 14'. In order to provide the one or more lateral holes 14', the securing plate 7 may be configured with one or more lateral protrusions 21 having a rounded shape. The lateral protrusions 21 may be provided with a respective lateral threaded hole 14' for a respective tilting preventing means 6. However, it should be understood that an alternative to providing the securing plate 7 with the protrusions 21 in order to accommodate the lateral holes 14', is to make the securing plate 7 wider to accommodate the one or more lateral threaded holes 14'. Thus, the width of the securing plate 7 may be adapted to accommodate the one or more lateral threaded holes 14'.

As schematically illustrated in FIG. 5A, the one or more lateral threaded holes 14' may be arranged along a line S-S that intersects the center of the respective threaded hole 14' and intersects the longitudinal axis L-L. An angle β may be provided between the line S-S and the longitudinal axis L-L. For example, the angle β may be in the range of 5 to 15 degrees, and in some embodiments the angle β is about 10 degrees. Further, the one or more lateral threaded holes 14' may be located at a distance d,d-1,d-2 from the longitudinal axis L-L. The distance d,d-1,d-2 may be approximately 5 mm.

It should be understood that in case of two lateral holes 14'-1,14'-2, the first lateral hole 14'-1 may be arranged at a first distance d-1 from the longitudinal axis L-L, and the second lateral hole 14'-2 may be arranged at a second distance d-2 from the longitudinal axis L-L. Further, it should be understood that the first and second distances d-1,d-2, may be the same distance but they don't have to be the same distance.

The provision of a securing plate 7 having lateral threaded holes 14' arranged in the second end portion 15 laterally of the longitudinal axis L-L of the securing plate 7 and at opposite sides of the longitudinal axis L-L, as shown in FIGS. 5A-5C, enables a more flexible use of the securing plate 7 since the securing plate 7 thanks to the lateral threaded holes 14' may be adjusted to fit for fixation of bone fragments at a bone fracture irrespective of whether the bone fracture is in a left femur or a right femur. It should be understood that when the securing plate 7 is placed at the correct position for fixation of the bone fragments, one tilting preventing means 6 is arranged in only one of the lateral threaded holes 14' to provide fixation and to prevent tilting.

The embodiments illustrated in FIGS. 5A and 5C, do not comprise any threaded holes 14 located along the longitudinal axis L-L in the second end portion 15 of the securing plate 7. However, it should be understood that also the embodiments illustrated in FIGS. 5A-5C comprising one or more lateral holes 14' also may comprise one or more central holes 14, e.g. holes 14 located with its center on the longitudinal axis L-L. Thus, some embodiments of the securing plate 7 comprise only the lateral threaded holes 14' arranged at a distance from the longitudinal axis L-L while other embodiments comprise one or more of the threaded holes 14 in addition to the lateral threaded holes 14'.

It should be understood that even if the triangular shape of the first end portion 11 of the securing plate 7 in FIGS. 4A and 4C is arranged symmetrically around the longitudinal axis L-L it should be understood that the triangular shape of the first end portion 11 of the securing plate 7 may be angled in relation to the longitudinal axis of the securing plate 7, e.g. the first end portion 11 may be tilted in relation to the shaft, e.g. the second end portion 15, of the securing plate 7.

Further modifications of the present invention within the scope of the appended claims are feasible without departing from the idea and object of the invention. As such, the present invention should not be considered as limited by the described embodiments thereof and the figures illustrating these embodiments. Rather, the full scope of the invention should be determined by the appended claims with reference to the description and the drawings. Thus, the device according to the present invention may of course comprise more than three fixation means 5 and more than one or two tilting preventing means 6 and the securing plate may be configured with a corresponding number of threaded holes 10, 14 for said means. The fixation means 5 and the tilting preventing means 6 may be configured differently from what is described above and illustrated in the drawings.

The invention claimed is:

1. A device for fixation of bone fragments at a vertical femoral neck fracture (4),
    which device (1) comprises at least three fixation means (5) and a securing plate (7),
    which at least three fixation means (5) each comprises:
    a first fixing portion (8) which is configured for fixing the fixation means (5) in an inner bone fragment (2),
    a second fixing portion (9) with threads for locking the fixation means (5) in substantially parallel holes (10) with threads in a first end portion (11) of the securing plate (7), said securing plate (7) being configured for engagement of an outside surface of an outer bone fragment (3) without fixed connection therewith, and
    a middle portion (12) which is situated between the first and second fixing portions (8, 9), wherein the device in said middle portion (12) has a smooth unthreaded exterior, and is configured to run through the outer bone fragment (3), whereby during secondary compression of the inner and outer bone fragments (2, 3) due to forces, particularly downwardly and rearwardly directed rotational forces, applied thereto, the smooth unthreaded exterior of the middle portion (12) allows a sliding movement of the at least three fixation means (5) and said outer bone fragment (3) relative to one another along a respective longitudinal axis of the at least three fixation means (5) thereby allowing an interruption of the engagement of the securing plate (7) with the outer bone fragment (3) without affecting the angular position of the fixation means (5) relative to the securing plate (7) and relative to one another,
    wherein the at least three fixation means (5) and the securing plate (7) are all configured to be without fixed connection to the outer bone fragment (3) and wherein the device is further comprising:
    at least one tilting preventing means (6) consisting of
    a fixing portion (13) with threads for locking the tilting preventing means in a hole (14; 14',14'-1,14'-2) with threads in a second end portion (15) of the securing plate (7) opposite to said first end portion (11) thereof, said hole (14; 14',14'-1,14'-2) being substantially parallel with the holes (10) for the fixation means (5); and
    an engagement portion (16) having a smooth unthreaded exterior which is configured to extend into the outer bone fragment (3) without fixed connection therewith and configured to allow, during said secondary compression of the inner and outer bone fragments (2, 3), a sliding movement of the at least one tilting preventing means (6) and said outer bone fragment (3) relative to one another along a longitudinal axis of the at least one tilting preventing means (6) and thereby allowing an interruption of the engagement of the securing plate (7) with the outer bone fragment (3), and yet preventing or counteracting tilting of the device (1) due to forces trying to cause tilting, particularly varus tilting, of the inner bone fragment (2).

2. Device according to claim 1, wherein the first end portion (11) is configured with the threaded holes (10) arranged in a substantially triangular pattern, which triangular pattern is angled an angle (a) relative to a longitudinal axis (L-L) of the securing plate (7), and wherein the angle (a) is in the range of 5 to 15 degrees, preferably around 10 degrees.

3. Device according to claim 1, wherein the second end portion (15) is configured with one or more lateral threaded holes (14', 14'-1,14'-2) arranged laterally of the longitudinal axis (L-L) of the securing plate (7).

4. Device according to claim 1, wherein the engagement portion (16) of said at least one tilting preventing means (6) is configured to run through the outer bone fragment (3) from the lateral side thereof to the opposite medial side.

5. Device according to claim 4, wherein the engagement portion (16) of said at least one tilting preventing means (6) is configured with such length that it can run through the outer bone fragment (3) from the lateral side thereof to the opposite medial side and yet protrude therefrom by about 4-8 mm.

6. Device according to claim 1, wherein the device (1) comprises two tilting preventing means (6) and the securing plate (7) of the device is configured with two threaded holes (14, 14', 14'-1,14'-2) for said tilting preventing means.

7. Device according to claim 1, wherein the first end portion (11) of the securing plate (7) has a substantially triangular shape with the holes (10) for the at least three fixation means (5) arranged in the substantially triangular pattern.

8. Device according to claim 1, wherein the holes (10) for the at least three fixation means (5) and the hole or holes (14,14';14'-1,14'-2) for the tilting preventing means (6) are all configured to run obliquely through the securing plate (7).

9. Device according to claim 1, wherein each tilting preventing means (6) is configured as a peg with a fixing portion (13) in the form of a threaded end portion.

10. Device according to claim 1, wherein each fixation means (5) is configured as a bone screw with a first fixing portion (8) in the form of a threaded forward end portion of the bone screw.

11. Device according to claim 1, wherein each fixation means (5) is configured as a bone nail comprising a sleeve (17) and disposed therein, a pin (18) arranged for movement in the sleeve so that at least a forward portion (19) of the pin can be driven outwards through at least one lateral opening (20) in the sleeve, said forward portion constituting a first fixing portion (8) in the form of at least one hook which engages in the inner bone fragment (2).

12. Device according to claim 1, wherein the middle portions allow the sliding movement when the first fixing portions are fixed to the inner bone fragment and the second fixing portions are fixed to the securing plate.

\* \* \* \* \*